United States Patent [19]

Pettit

[11] 4,306,084
[45] Dec. 15, 1981

[54] ALCOHOL AND ALDEHYDE PRODUCTION USING RUTHENIUM CARBONYL CATALYSTS

[75] Inventor: Rowland Pettit, Austin, Tex.

[73] Assignee: The University of Texas, Austin, Tex.

[21] Appl. No.: 124,436

[22] Filed: Feb. 25, 1980

Related U.S. Application Data

[63] Continuation of Ser. No. 967,038, Dec. 6, 1978, abandoned.

[51] Int. Cl.³ .................. C07C 45/50; C07C 29/16
[52] U.S. Cl. .................. 568/451; 568/455; 568/882; 568/909
[58] Field of Search .............. 568/451, 882, 909, 452, 568/453, 455

[56] References Cited

U.S. PATENT DOCUMENTS

| | | | |
|---|---|---|---|
| 3,020,314 | 2/1962 | Alderson | 568/909 |
| 3,636,159 | 1/1972 | Solomon | 568/455 |
| 3,929,900 | 12/1975 | Schnur et al. | 568/453 |
| 3,933,919 | 1/1976 | Wilkinson | 568/454 |
| 3,984,478 | 10/1976 | Homeier | 568/455 |
| 4,098,727 | 7/1978 | Haag et al. | 568/451 |
| 4,226,845 | 10/1980 | Laine | 568/882 |

*Primary Examiner*—Werren B. Lone
*Attorney, Agent, or Firm*—Ned L. Conley; Murray Robinson; David A. Rose

[57] ABSTRACT

The present invention is an isomerically specific improvement of the oxo process reaction. It comprises the reaction of an olefin with carbon monoxide and water or hydrogen in a basic solution in the presence of a ruthenium carbonyl catalyst to preferentially produce the next higher normal aldehyde, or alcohol.

5 Claims, No Drawings

ALCOHOL AND ALDEHYDE PRODUCTION USING RUTHENIUM CARBONYL CATALYSTS

This is a continuation of application Ser. No. 967,038 filed Dec. 6, 1978, now abandoned.

BACKGROUND OF THE INVENTION

1. Field of the Invention

The present invention relates generally to the production of aldehydes and alcohols from olefins and more specifically to the production of normal alcohols from the reaction of olefins, carbon monoxide and water or hydrogen in the presence of a ruthenium carbonyl catalyst.

2. Background of the Prior Art

A. Hydroformylation

Originally the conversion of olefins into aldehydes or alcohols, depending upon temperature, was observed during investigations of the Fisher-Tropsch process. Fundamentally, this reaction entails the conversion of an olefin into an aldehyde by catalytic reaction of the olefin with a synthesis gas. The synthesis gas is a mixture of carbon monoxide and hydrogen. The catalyst is a metal complex, generally a cobalt carbonyl.

When carried out in conditions that result in the formation of aldehydes, the reaction is called "hydroformylation", i.e. reaction 1.

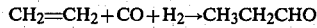

$$CH_2=CH_2 + CO + H_2 \rightarrow CH_3CH_2CHO \tag{1}$$

Although other metal catalysts can be used in hydroformylation, it is customarily performed using either dicobalt octacarbonyl, or the catalyst is formed in situ from a cobalt salt or cobalt metal. The reaction temperatures employed are normally in the range of from 100° C. to 120° C. If it is desired to produce alcohols, higher temperatures, i.e., from 150° C. to 180° C., cause reduction of the aldehyde to an alcohol. The prior art teaches that this hydroformylation should be performed at a relatively high pressure, i.e., between 200 and 300 atmospheres.

A comprehensive study of the hydroformylation reaction is found in Chapter 6 of *Transition Metal Intermediates in Organic Synthesis*, by C. W. Bird, which was published in 1967 and is distributed in the United States by Academic Press, Inc., 111 Fifth Avenue, New York, New York 10003. The Library of Congress card number for this treatise is 67-21471. In the interest of brevity, the entirety of Chapter 6, i.e. from page 117 to 148, inclusive, is hereby incorporated by reference into this application. A copy of this chapter is provided with the application for the convenience of the Examiner and will form a portion of the file wrapper of this application.

The reaction mechanism of the hydroformylation reaction is extremely complex and has not been fully elucidated. Because of its industrial importance in the production of aldehydes and alcohols, which are used commercially as plasticizers, many workers have studied the hydroformylation reaction hoping to experimentally discover catalysts and reaction conditions that would overcome some of the limitations of the prior art. The major limitations are the tendency to generate a relatively high percentage of undesirable iso or branched isomer of the product as low conversion efficiency. The prior art teaches that the hydroformylation efficiency increases as the catalyst is changed from iridium, to cobalt and then to rhodium compounds. Rhodium catalysts are from 100 to 1,000 times more effective than cobalt catalysts. Unfortunately, all prior art rhodium catalysts require the addition of a large amount of co-catalyst such as triphenylphosphine ($Ph_3P$) to achieve an acceptable, i.e., around 7:1, ratio of normal to branched products. Rh catalysts can only be used economically to make relatively low molecular weight aldehydes and alcohols because these products must be distilled from the reaction mixtures and the temperature of the distillation cannot exceed the breakdown temperature of the Rh catalyst, which is relatively low. Rhodium catalysts do, however, catalyze the hydroformylation reaction at relatively low temperatures and pressures, i.e., around 55° C. and 90 atmospheres. At higher temperatures, i.e. around 100° C., the aldehydes are reduced to alcohols. Commercial aldehyde and alcohol production desires the production of normal, as opposed to iso products. The prior art teaches that rhodium catalysts produce larger amounts of branched chain aldehydes and cause more double-bond migration than cobalt or iron catalysts.

The prior art also teaches that ruthenium catalysts are not desirable in the hydroformylation reaction. Not only do they produce an unacceptable amount of iso products under reaction conditions taught by the prior art, but ruthenium catalysts also have been cited for their low conversion efficiencies. (See page 138 of Bird, cited above.)

B. Reppe Modification

Around 1953 W. Reppe published the Reppe modification of the hydroformylation reaction. As we discussed above, in the normal reaction an olefin is converted to the next higher aldehyde or alcohol through reaction with carbon monoxide and hydroxide at high pressure in the presence of a cobalt or rhodium carbonyl catalyst. In the Reppe modification, the same conversion is achieved without the use of molecular hydrogen by reaction of the olefin with carbon monoxide and water in the presence of an iron carbonyl catalyst together with a Bronsted or Lewis base. This result was unexpected because iron carbonyl is a very poor catalyst for the hydroformylation reaction in gaseous hydrogen, whereas, under Reppe's conditions, i.e., with $H_2O$ and CO, iron carbonyl becomes an active catalyst at relatively mild temperatures and pressures, i.e. 100° C. and 500 psi. Unfortunately, the iron carbonyl catalyzed Reppe modification of the hydroformylation reaction cannot be commercially important both because it produces a high percentage of undesirable iso-aldehydes and alcohols and because of its relatively low conversion efficiency. To the best of the applicant's knowledge, no successful commercial use has been made of ruthenium catalysts in either the normal or the Reppe modification of the hydroformylation reaction.

SUMMARY OF THE PRESENT INVENTION

The present invention teaches an isomerically specific method of producing the next higher normal alcohol from the reaction of an olefin under normal and Reppe conditions by conducting the reaction in a basic medium in the presence of a ruthenium carbonyl catalyst.

Specifically, for the Reppe modification, a normal olefin is reacted at moderate temperature, i.e., in the range of 100°–150° C., and moderate pressure, i.e. in the range of 200–1200 psia, in the presence of a ruthenium carbonyl catalyst at a pH of between 11 and 8. The reaction product is predominantly the normal isomer. Unlike what would logically be expected from prior art, ruthenium catalysts under Reppe conditions in basic solutions can yield a normal to iso aldehyde and alcohol ratio of about from 10:1 to 50:1. Present industrial processes require a phosphine additive to yield a 7:1 ratio of normal product to the undesirable iso form. It should be noted that ruthenium compounds are less expensive than equivalent rhodium compounds.

It therefore is a purpose of the present invention to provide a method of economically producing normal aldehydes and alcohols.

It is a further purpose of the present invention to allow the production of normal aldehydes and alcohols from olefins wherein the ratio of normal to iso forms in the product is greater than 10:1 and the reaction conditions required for the synthesis are mild.

It is a further purpose of the present invention to provide a method of making normal aldehydes and alcohols from olefins that do not require the use of phosphine.

Other and further objects of the present invention may be determined by those skilled in the art through reading the following description of the preferred embodiment and appended claims.

DESCRIPTION OF THE PREFERRED EMBODIMENT

The Normal Oxo Reaction and the Invention

The normal oxo reaction can be performed with a ruthenium catalyst in a basic solution to yield a very high normal to branched product ratio without the addition of phosphines.

Specific Example #1: Normal Conditions With $Ru(CO)_{12}$ Catalyst and Base

A 310 mL autoclave was charged with 6.4 mg (0.010 mmol) $Ru_3(CO)_{12}$ and 3.0 g $Na_2CO_3$. Autoclave was chilled and purged with argon. A chilled solution consisting of 5.15 g 1-butene, 20 g water and sufficient 1,2-dimethoxyethane to bring volume to 100 mL was added. Autoclave was sealed, then purged twice with 200 psi CO, pressurized to 400 psi CO, then pressurized to 1000 psi using $H_2$. Autoclave was heated to 140° C. and maintained at that temperature for ten hours. After chilling to 0° C., gas analysis indicated essentially the same $CO/H_2$ ratio at the end of the reaction as in the beginning, as well as little isomerization and hydrogenation of the 1-butene. Analysis of the liquid phase indicated 4.8 mmol pentanal, 0.4 mmol 2-methylbutanal and 0.1 mmol pentanol.

The Reppe Modification and the Invention

Discussion

During research conducted to understand the manner in which iron carbonyl catalysts use carbon monoxide and water in place of hydrogen for reduction, and with the expectation that this understanding would be of value for the design of catalysts and other reductions using carbon monoxide and water, the applicant investigated the mechanism of the Reppe modification of the hydroformylation reaction.

The applicant found that the formation of alcohols under Reppe conditions is strongly dependent on the pH of the solvent medium.

For example, when 10 grams of iron carbonyl is heated in 300 milliliters of a 3.3% aqueous potassium hydroxide solution to 100° C. in a L-1 autoclave under a pressure of 200 psi of ethylene and 300 psi of carbon monoxide, the iron carbonyl dissolves and forms anion 1 according to reaction 2.

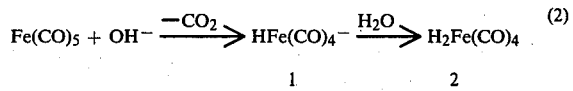

$$Fe(CO)_5 + OH^- \xrightarrow{-CO_2} HFe(CO)_4^- \xrightarrow{H_2O} H_2Fe(CO)_4 \quad (2)$$
$$\qquad\qquad\qquad\qquad\qquad 1 \qquad\qquad\qquad 2$$

The pH of the resulting solution is initially 12.0 and infrared spectral analysis indicates that anion 1 is the only metal carbonyl species present. As heating continues, the pH of the solution decreases owing to the reaction of carbon monoxide with hydroxide ion to produce formate ion. However, only when the pH drops to the vicinity of 10.7 does consumption of ethylene and formation of propanol being to occur. At this point, the principal metal carbonyl anion present is the species 1, although the solutions are frequently red in color indicating the presence of at least trace amounts of the trinuclear anion $HFe_3(CO)_{11}^-$. The formation of proponal continues as the pH finally lowers to around 8.0.

In an identical experiment, but with acetaldehyde added to the reaction mixture at pH 12.0, it is found that the acetaldehyde is immediately reduced to ethanol at the high pH, but, again, only when the pH drops to 10.7 does the ethylene react to form propanol.

These data indicate that, whereas the anion 1 is capable of reducing aldehydes, it is not capable of interacting with olefins; i.e., at pH 10.7 the conjugate acid of 1, i.e., species 2, begins to be formed in significant concentration and this species 2 is the one that undergoes initial reaction with the olefin. Consistent with this proposal we find that, when 1,5-cyclooctadiene is stirred with a solution of $KHFe(CO)_4$ in aqueous $K_2CO_3$ under an argon atmosphere at a pH initially of 12.0, and the pH then lowered by the addition of a stream of $CO_2$, the pH must be lowered to 10.7 for the isomerization of 1,5- to 1,3-cyclooctadiene to occur. It is known that 2 is a powerful catalyst for double-bond isomerization reactions. In a similar experiment, in which the initial solution contained the $HFe_3(CO)_{11}$ anion, no isomerization of 1,5-cyclooctadiene occurred in the pH range of 12.0–8.0. Although the trinuclear anion may be observed in the Reppe modification, it is not a catalyst under the reaction conditions.

Also consistent with the proposed role of 2 is the fact that, in the absence of olefins, basic solutions of the anion 1 under a pressure of CO begin to liberate molecular hydrogen when the pH is lowered to the vicinity of 10.7. The species 2 is known to decompose readily with liberation of $H_2$. On the basis of these data, and by analogy with the mechanism of the normal reaction using $HCo(CO)_4$ as given by Heck and Beslow, the applicant believes that the mechanism of the Reppe modification involves reaction of an olefin with 2 to generate an alkyl metal hydride derivative and the subsequent elimination of the aldehyde. The $Fe(CO)_4$ which is liberated reacts with CO to give $Fe(CO)_5$, thus completing the catalytic cycle. Depending on conditions the aldehyde may be further reduced to the alcohol.

The applicant believes the above described mechanism is accurate, but regardless of whether or not this is the actual mechanism of the Reppe modification, the present invention, i.e., the processes performed as described below in this specification, obtains the desired results.

The normal hydroformylation reaction and the Reppe modification of it appear to be mechanistically closely related; the essential point in the latter process is that it is easier to form the species $H_2Fe(CO)_4$ from the reaction of $Fe(CO)_5$ and water plus a base than it is from $Fe(CO)_5$ and molecular hydrogen; for this reason the combination of water and CO provides a superior reducing system than does molecular hydrogen in this instance.

Directed by these conclusions the applicant discovered other metal carbonyl systems which are much superior to $Fe(CO)_5$ in effecting the hydroformylation reaction using $CO+H_2O$ in place of $H_2$. Because of the formation of $CO_2$, one requirement for a metal carbonyl to be a catalyst of practical value in the Reppe modification, in a catalytic cycle as given above for $Fe(CO)_5$, is that it must be capable of generating a metal hydride species through attack by a weak base. The base must be weak enough such that it can be regenerated from its carbonate salt upon moderate heating. Of the mononuclear metal carbonyls only $Fe(CO)_5$ appears to meet this requirement. However, $Ir_4(CO)_{12}$ and $Rh_6(CO)_{16}$ are readily attacked by mild base to generate metal carbonyl hydride anions, and they, together with several other polynuclear carbonyls have been tested as hydroformylation catalysts with $CO+H_2O$. The pertinent data as applied to the reaction of propylene+$CO+H_2O$ to give n- and isobutyraldehyde are given in Table I, together with comparable data using $Fe(CO)_5$. (It should be noted that the exact nature of the catalyst species present under the reaction conditions has not yet been established.)

If the polynuclear carbonyls catalyze the reaction in a manner similar to that described for $Fe(CO)_5$, then, in the absence of olefin, they could also be catalysts for the generation of hydrogen via the water gas shift reaction; i.e., $CO+H_2O \rightarrow CO_2+H_2$. Hydrogen formation would be expected to occur via the steps given in equation 3. This catalytic generation of hydrogen is indeed observed. The final column of Table I gives the efficiency of the generation of hydrogen for each catalyst under the same conditions as was used in the hydroformylation reaction, except for the exclusion of olefin.

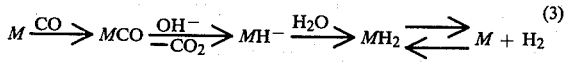

$$M \xrightarrow{CO} MCO \xrightarrow[-CO_2]{OH^-} MH^- \xrightarrow{H_2O} MH_2 \rightleftharpoons M + H_2 \quad (3)$$

From Table I it is seen that catalysts which are efficient for the hydroformylation reaction are also efficient for the water gas shift reaction, but the converse is not always true.

It should be noted that all the experiments whose results are recorded in Table I were run for 10 hours in a 300 milliliter stirred autoclave containing 0.05 millimole of catalyst, 22 milliliters of 25% aqueous trimethylamine, 78 milliliters of THF, 350 psi of carbon monoxide, and 150 psi of propylene. Small amounts of propane were formed in experiments 2, 5, 6, 7 and 8.

Specific Example #2: Reppe Using $Ru_3(CO)_{12}$ and Base

A magnetically stirred 0.3 L autoclave was charged with 32 mg (0.050 mmol) $Ru_3(CO)_{12}$, and while purging with CO, a chilled solution consisting of 5.15 g 1-butene, 20 g 25% trimethylamine in water and sufficient 1,2-dimethoxyethane to bring volume to 100 mL. Autoclave pressurized to 750 psi CO. Autoclave was heated to an average temperature of 100° C. over a ten hour reaction period. At the end of reaction period, autoclave cooled in ice-bath to 0° C. Gas analysis indicated 56%, 30% CO, 12% $CO_2$, and 2% hydrocarbon; the hydrocarbon consisted of 2% each of cis- and trans-2-butene, 1.5% butane, the remainder being 1-butene. Liquid analysis indicated 1.45 mmol pentanal, 0.073 mmol 2-methylbutanal and 0.183 mmol pentanol. (n/b) ratio=20.

Specific Example #3: Reppe with $Ru_3(CO)_{12}$ Catalyst Without Base

Conditions same as Example #2, except water and trimethylamine were deleted, and that 500 psi each of CO and $H_2$ were used in place of the 750 psi CO; (n/b) ratio=2.9.

It will easily be seen that the base is critical for the Ru catalyzed reaction to achieve a high normal to branched product ratio.

Specific Example #4: Reppe Conditions With $H_4Ru_4(CO)_{12}$ Catalyst and Base

A 310 mL autoclave was charged with 37.2 mg (0.050 mmol) $H_4Ru_4(CO)_{12}$. A high pressure liquid pump was connected to autoclave. Autoclave was purged with carbon monoxide, pressurized to 150 psi with propylene and then to 500 psi with CO. At this point a solution consisting of 20 g of 25% trimethylamine in water, diluted to 100 mL with tetrahydrofuran, was pumped into autoclave via high pressure pump. Autoclave was stirred and heated to 100° C. At the end of 10 hours, autoclave cooled in water bath and gas sample removed for analysis. The gas phase consisted of 60% $H_2$, 25% CO, 8% $CO_2$ and 5% propylene; little hydrogenation of propene was observed. The reaction solution was analyzed and was found to consist of 4.0 mmol butanal, 0.36 mmol 2-methylpropanal and 0.10 mmol butanol.

TABLE I

| Experiment No. | Catalyst Compound | Temperature in °C. | Mol of $C_4$ aldehyde per mol of catalyst | n-/isoaldehyde ratio | $C_4$ aldehyde/ $C_4$ alcohol | Water gas shift reaction, mol of $H_2$/mol of catalyst |
|---|---|---|---|---|---|---|
| 1 | $Fe(CO)_5$ | 110 | 5.2 | 1.0 | 4.5 | 5 |
| 2 | $Rh_6(CO)_{16}$ | 125 | 300 | 1.4 | 40 | 1700 |
| 3 | $Ru_3(CO)_{12}$ | 100 | 47 | 11.5 | 43 | 3300 |
| 4 | $H_4Ru_4(CO)_{12}$ | 100 | 79 | 11.0 | 37 | 3400 |
| 5 | $Os_3(CO)_{12}$ | 180 | 13 | 1.9 | 6.6 | 270 |
| 6 | $H_2Os_3(CO)_{10}$ | 180 | 6 | 1.2 | 300 | 270 |
| 7 | $H_4Os_4(CO)_{12}$ | 180 | 9 | 1.4 | 300 | 400 |
| 8 | $Ir_4(CO)_{12}$ | 125 | 250 | 1.8 | 300 | 300 |
| 9 | $(Bu_4N)[Pt_3(CO)_6]_5$ | 125 | 0.5 | 1.9 | | 700 |

Specific Example #5: Reppe Conditions With Ru₃(CO)₁₂ and Base

A 310 mL autoclave was charged with 32 mg (0.05 mmol) $Ru_3(CO)_{12}$. Autoclave was chilled in ice-methanol and purged with argon. To the autoclave was added a cold solution consisting of 5.15 g (92 mmol) 1-butene, 20 g of 25% trimethylamine in water, and enough 1,2-dimethoxyethane to bring volume to 100 mL. Autoclave was sealed, pressurized to 750 psi carbon monoxide, and heated to 100° C. During the course of the reaction, the autoclave pressure was observed to increase, due to concomitant hydrogen production. At the end of ten hours, autoclave was cooled to 0° C. in ice-bath and gases sampled; found 53% $H_2$, 34% CO, 10% $CO_2$, and 3% hydrocarbon in gas phase. The gas phase hydrocarbon was further analyzed to consist of approximately 2% each of cis- and trans-2-butene, 1% butene, the remaining being 1-butene. The liquid phase was analyzed by gas-liquid phase chromatography and was found to consist of 3.90 mmol pentanal, 0.08 mmol 2-methylbutanal and 0.096 mmol pentanol.

Although the experiments described above teach specific reaction times, temperatures, pressures and stoichiometric ratios, it should be understood that this was done so that applicant could conveniently compare the test results from each experiments. Those skilled in the art can make many obvious changes in these reaction conditions without departing from the scope of the present invention. Also, many ruthenium compounds other than the specific ones tested in these experiments may be used to catalyze the reaction or form the catalyst in situ from a ruthenium salt or ruthenium metal. Some examples of these compounds are:

Ru, $RuCl_3$, $RuO_2$, $RuO_4$

The above described specific examples, which represent the experimental data illustrating the best mode of practice of the present invention now known to the applicant, should not be read as limiting the present invention. Rather the process claimed as the present invention should be limited only by the appended claims and their equivalents.

I claim:

1. In the hydroformylation of olefins for the preparation of aldehydes and alcohols by reacting carbon monoxide, hydrogen and an olefin in the presence of a catalyst consisting of ruthenium carbonyl, the improvement which comprises
   conducting the hydroformylation reaction at a pH of from about 11 to about 8,
   whereby predominantly straight chain aldehydes and alcohols are formed.

2. A process as defined by claim 1 wherein the catalyst is formed in situ from a material selected from a group consisting of ruthenium, its salts and its oxides.

3. In the production of an aldehyde by the hydroformylation of an olefin comprising reacting an olefin, carbon monoxide and hydrogen in the presence of a material selected from the group consisting of ruthenium, ruthenium salts, ruthenium oxides and ruthenium carbonyls, the improvement which comprises
   conducting the hydroformylation reaction at a pH of from about 11 to about 8,
   substantially in the absence of any other catalyst,
   whereby a predominantly normal as opposed to branched chained aldehyde is formed.

4. A process as defined in claim 3 in which the reaction is carried out at a pressure of from about 200 to about 1200 psi.

5. A process as defined by claim 4 in which the reaction is carried out at a temperature of from about 100° C. to about 150° C.

* * * * *